United States Patent [19]

O'Boyle

[11] Patent Number: 4,634,424

[45] Date of Patent: Jan. 6, 1987

[54] MULTIPLE RE-ENTRY IMPLANTABLE SEPTUM AND METHOD OF USING SAME

[75] Inventor: Matthew O'Boyle, Somers, Conn.

[73] Assignee: Windsor Medical, Inc., Enfield, Conn.

[21] Appl. No.: 603,149

[22] Filed: Apr. 23, 1984

[51] Int. Cl.$^4$ .............................................. A61M 31/00
[52] U.S. Cl. ........................................ 604/51; 604/86
[58] Field of Search ................................ 604/8–10, 604/49, 29, 175, 891, 415, 896, 86; 128/1 R

[56] References Cited

U.S. PATENT DOCUMENTS

| | | | |
|---|---|---|---|
| 3,310,051 | 3/1967 | Schulte | 604/175 |
| 3,402,710 | 9/1968 | Paleschuck | 128/1 R |
| 3,682,315 | 8/1972 | Haller | 604/415 |
| 3,783,868 | 1/1974 | Bokros | 604/896 X |
| 3,853,127 | 12/1974 | Spademan | 604/175 X |
| 4,014,328 | 3/1977 | Cluff et al. | 128/760 |
| 4,177,814 | 12/1979 | Knepsheild et al. | 604/175 X |
| 4,190,040 | 2/1980 | Schulte | 128/1 R |
| 4,190,048 | 2/1980 | Sampson | 604/175 |
| 4,193,397 | 3/1980 | Tucker et al. | 604/56 |
| 4,256,102 | 3/1981 | Monaco | 604/175 |
| 4,258,711 | 3/1981 | Tucker et al. | 604/56 |
| 4,338,934 | 7/1982 | Spademan | 604/167 |
| 4,360,019 | 11/1982 | Portner et al. | 604/131 |
| 4,400,169 | 8/1983 | Stephen | 604/49 |
| 4,405,305 | 9/1983 | Stephen et al. | 604/49 |
| 4,436,519 | 3/1984 | O'Neill | 604/175 |

*Primary Examiner*—John D. Yasko
*Attorney, Agent, or Firm*—Antonelli, Terry & Wands

[57] ABSTRACT

An improved multiple re-entry implantable septum is disclosed. The septum comprises a casing and a resilient member positioned within the casing. The resilient member has a perforation therein which is compressed closed. An outer side of the casing presents a relatively large surface configured to channel the end of a slender, elongate component such as a needle to a predetermined location at a relatively small bore in the outer side of the casing. The small bore in the casing is located adjacent the perforation in the resilient member. An assembly of a first needle and a cannula positioned over the needle is inserted into the skin so that the end of the needle contacts the relatively large surface of the casing and is channeled to the small bore therein. The bore is dimensioned to prevent passage of the first needle through the casing. The first needle is withdrawn from the casing and skin leaving the plastic cannula in place adjacent the small bore. A second, relatively smaller blunt needle is inserted into the cannula and through the small bore of the casing and the perforation in the resilient member to permit filling an implanted drug reservoir for an implanted infusion device.

4 Claims, 6 Drawing Figures

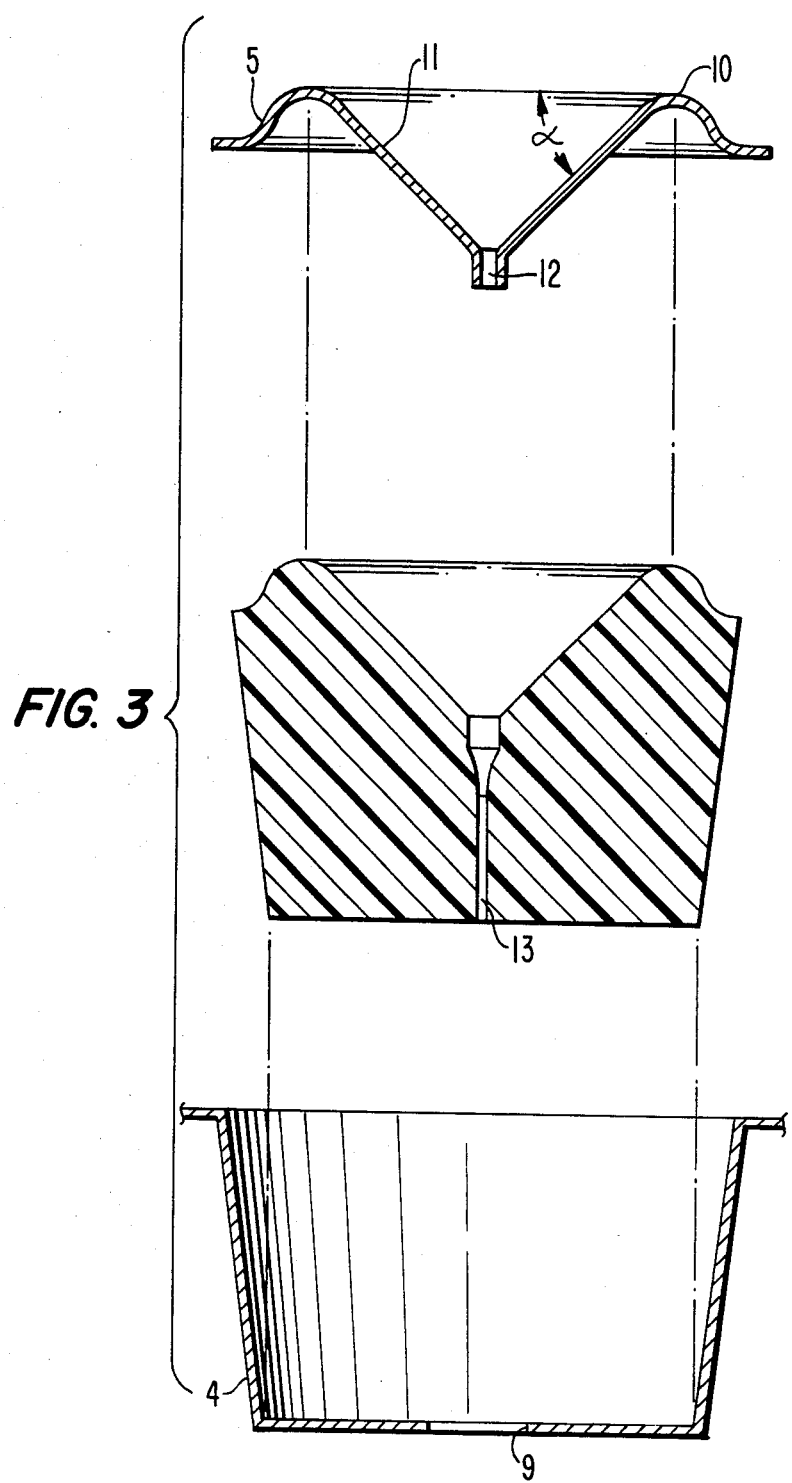

MULTIPLE RE-ENTRY IMPLANTABLE SEPTUM AND METHOD OF USING SAME

BACKGROUND AND SUMMARY OF THE INVENTION

The present invention is directed to a multiple re-entry implantable septum and a method of using the same. The implantable septum and method are suitable for use in conjunction with an implantable infusion device and the drug reservoir therefor.

With implantable infusion devices currently marketed, drugs to be infused into the human body are stored in a reservoir that is contained within a body cavity. To place drugs into the reservoir, it is necessary to pierce an inlet septum with a needle introduced percutaneously. The surface area of the septum available for puncture can be directly correlated to the ease of needle placement and the duration of time the septum can maintain its integrity. A large surface area will make locating of the septum under the skin easier; however, more stress will be applied to the resilient septum with each puncture than with a smaller surface area.

Certain currently available septa used in conjunction with implantable infusion devices consist of a solid piece of molded rubber force-fit into an inlet port, see U.S. Pat. Nos. 4,190,048; 4,193,397; and 4,360,019, for example. The force-fit assures that the rubber is placed in compression and, thus, punctures made through the rubber will be effectively sealed as the rubber expands to fill the space left by the passage of the needle. Such septa work well in limited use, disposable applications, but can become ineffective when repetitively punctured.

Chronic implantation of an infusion device will necessitate numerous punctures of the septum. Over an extended period of time, these perforations could result in uncontrolled and unmonitored leakage of the intended infusate through the septum into the body cavity. Depending upon the drug and its concentration, this situation could result in serious harm to the patient.

Thus, an object of the present invention is to provide an improved implantable septum which can be entered numerous times without compromising its mechanical stability or patient safety.

Another object of the invention is to provide an improved multiple re-entry implantable septum which can be easily located under the skin and which facilitates the placement of the needle into the septum.

These and other objects of the invention are attained by providing a multiple re-entry implantable septum comprising a casing and a resilient member positioned within the casing. The resilient member has a perforation therein which is compressed closed at least when the member is positioned within the casing. An outer side of the casing has a relatively large surface configured to channel the end of a slender, elongate component such as a needle to a predetermined location at a relatively small bore in the outer side of the casing which is located adjacent the perforation in the resilient member.

The size of the relatively small bore in the casing is smaller than the diameter of a needle of a first gauge so as to prevent the needle from passing through the bore, but is larger than a smaller diameter needle of a second gauge to permit the second needle to pass through the bore of the casing and the perforation of the resilient member.

In the disclosed embodiment, the casing is connected to an implantable drug reservoir for an implantable drug infusion device with multiple re-entry to the reservoir for filling the same being obtained via the small bore in the casing and the perforation in the resilient member. The resilient member is a silicone rubber or polyurethane molding perforated with a narrow bore hole. The resilient member is preferably force-fit into the casing so as to compress the member and close the bore hole therein.

The method of using the septum of the invention comprising providing an assembly of a first needle and a cannula positioned over the first needle, penetrating the skin with the first needle and cannula thereon and contacting the surface of the casing with the end of the needle so as to channel the needle to the small bore in the casing. The small bore is dimensioned to prevent passage of the first needle through the casing. The first needle is then withdrawn from the casing and skin, while leaving the cannula in place adjacent the small bore in the casing. A second, relatively smaller needle is then inserted into the cannula and through the small bore of the casing and the perforation in the resilient member. The second needle is attached to a syringe for filling the drug reservoir.

Since the needle will enter the septum through the same opening each time, and that opening will have been formed in the manufacturing process, no destruction of the silicone rubber or polyurethane member will occur due to punctures. In addition, the stress that is inflicted on the currently available septa due to punctures will be eliminated.

The protective shroud or casing over the resilient member also enables the implanted septum to be easily located under the skin and facilitates the placement of the needle into the septum. Therefore, the two most undesirable characteristics of implantable septum, material destruction leading to possible failure to contain liquid in the reservoir, and difficulty in locating the septum, are circumvented by the improved implantable septum of the invention.

These and other objects, features and advantages of the present invention will become more apparent from the following description when taken in connection with the accompanying drawings which show, for purposes of illustration only, one preferred embodiment in accordance with the present invention.

BRIEF DESCRIPTION OF THE DRAWINGS

FIG. 3 is a cross-sectional view of the multiple re-entry implantable septum of FIG. 1 and showing the component parts thereof in adjacent, disassembled relationship;

DESCRIPTION OF THE PREFERRED EMBODIMENT

Figure 1:
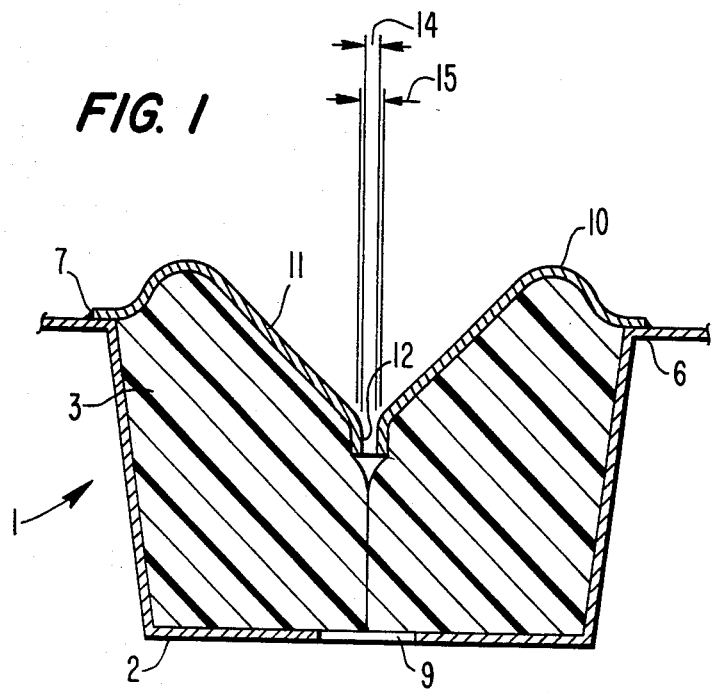
FIG. 1 is a cross-sectional view taken along the line II—II of the multiple re-entry implantable septum of FIG. 2.
Figure 2:
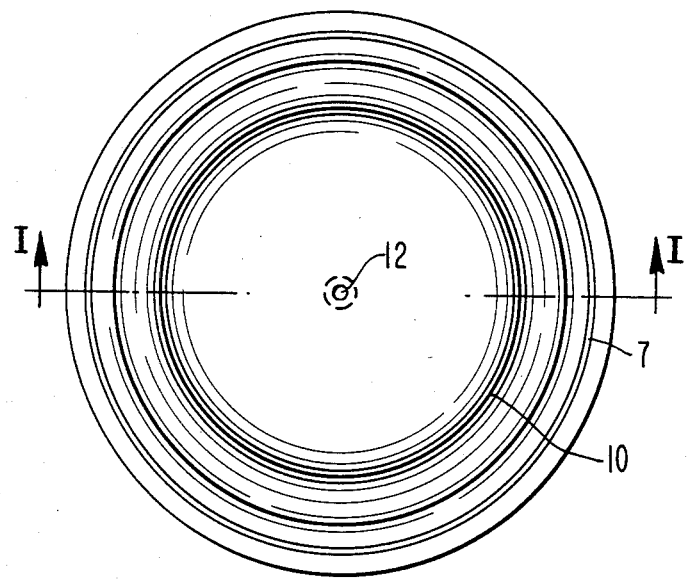
FIG. 2 is a top view of a multiple re-entry implantable septum according to a preferred embodiment of the invention.

Referring now to the drawings, a multiple re-entry implantable septum 1 of the invention comprises a casing 2 and a resilient member 3 positioned within the casing. The casing 2 is formed of a relatively rigid material such as stainless steel sheet metal having a thickness of 0.010 inch and includes a cup-shaped portion 4 for supporting the resilient member 3 and a protective shroud or cover 5, which is welded to the upper, outwardly extending flange 6 of the cup-shaped portion 4 by means of a seamless fillet weld 7, as depicted in FIGS. 1 and 2. The cup-shaped portion 4 is connected to, in this case formed integrally with, an implantable drum reservoir 8, illustrated in FIGS. 4A–4C. The bottom of the cup-shaped portion 4 includes a central opening or bore 9 through which a filling needle may pass, as discussed more fully hereinafter.

The protective shroud 5 of the casing 2 is dish-shaped with an outwardly protruding, circumferentially extending annular ridge 10 thereof being located about a funnel-shaped portion 11, which extends over most of the surface of the shroud for channeling the end of a slender, elongate component, such as a needle, to a predetermined location at the center of the shroud where a small bore 12 is provided. In the disclosed casing 2, the funnel-shaped portion 11 is angled downwardly from the plane of the ridge 10 at an angle α of 45°.

The resilient member 3 is formed of a molded silicon rubber or polyurethane material. The member 3 is perforated in the center with a narrow bore hole 13. The resilient member is dimensioned with respect to the casing 2 so that it must be force-fit into the casing to place the resilient material thereof under compression to close the bore hole 13 and form an effective seal between the drug reservoir and the body cavity.

The diameter of the small bore 12 in the shroud 5 of the casing 2 is such that a 24 gauge needle (0.0226 inch O.D.) is prevented from passing through the bore, while a smaller diameter needle of 27 gauge (0.0165 inch O.D.) can pass through the bore 12 and the perforation 13 of the resilient member 3 for filling the reservoir 8.

Figure 4A:
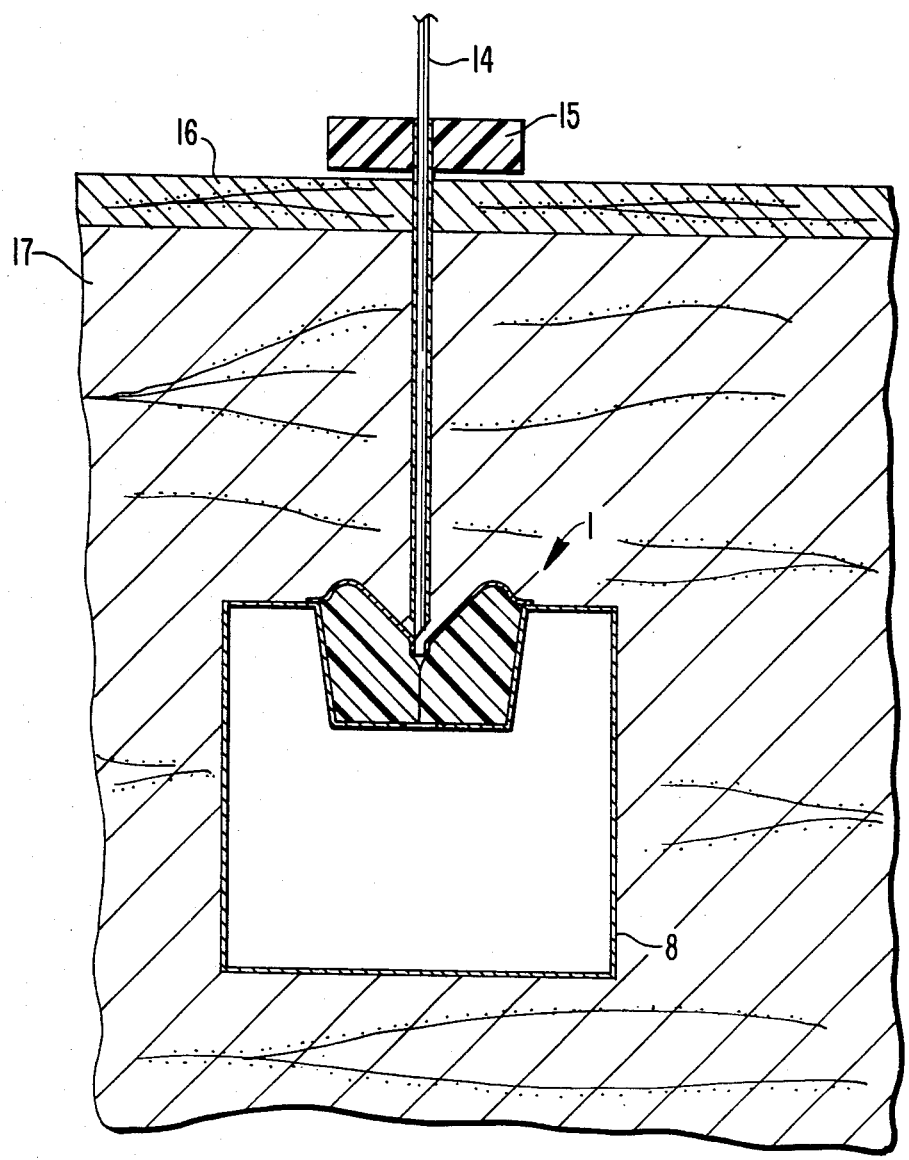
FIG. 4A is a schematic illustration of the septum of FIGS. 1-3 as a closure for an implanted drug reservoir with a 24 gauge needle and Teflon sleeve covering the needle being inserted into the body and toward the septum according to one step of the method of the invention.
Figure 4C:
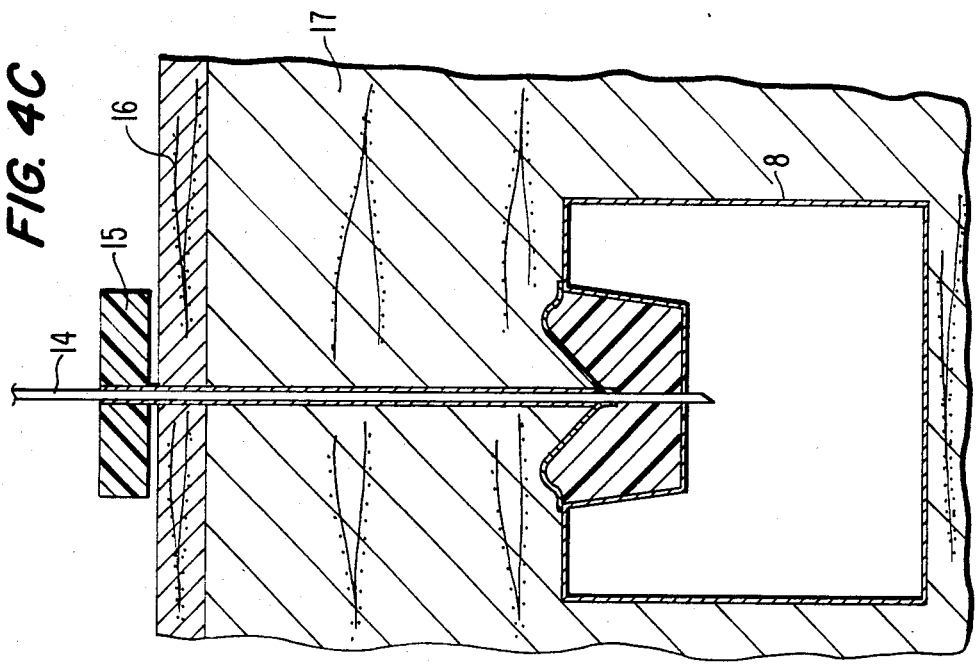
FIG. 4C is an illustration similar to FIG. 4B and showing a 27 gauge blunt cannula which has been passed through the Teflon sleeve and septum perforation to the implanted reservoir for filling the reservoir.
Figure 4B:
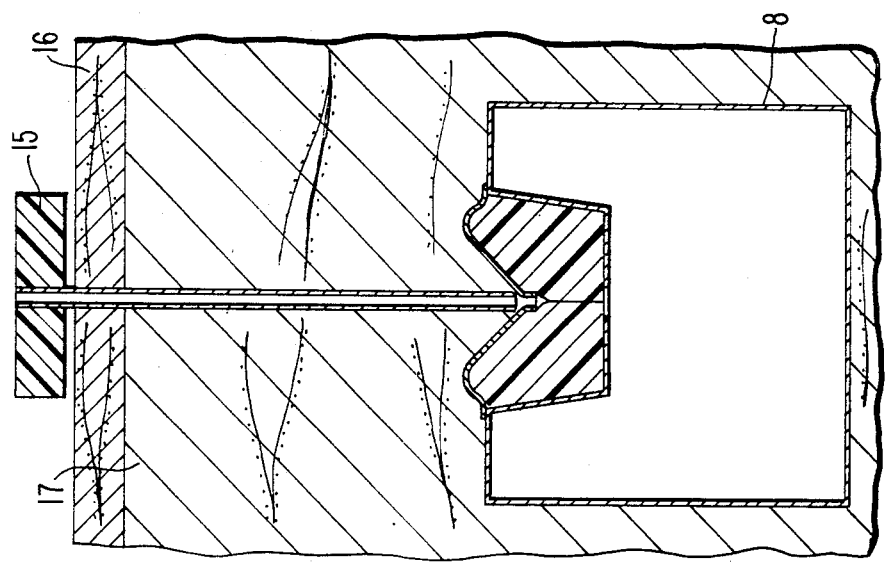
FIG. 4B is an illustration similar to FIG. 4A with the 24 gauge needle having been removed and showing the Teflon sleeve extending from the surface of the body to a position adjacent a perforation in the septum which is compressed closed.

According to the method of the invention, to fill the reservoir 8 with a drum to be dispensed by an implantable infusion device, an assembly of a 24 gauge needle with a beveled end and a Teflon cannula 15 covering the needle is inserted through the skin 16 and subcutaneous fat 17 so that the end of the needle 14 contacts the funnel-shaped portion 11 of casing 2 and is channeled to the small bore 12 therein, which prevents the passage of the needle 14 through the bore, see FIG. 4A. The needle 14 is then withdrawn from the skin, leaving the cannula 15 in place adjacent the bore 12 of the casing, as shown in FIG. 4B. A relatively smaller needle 16, particularly a 27 gauge blunt cannula, is then inserted into the Teflon cannula 15 and through the small bore 12 and the perforation 13 in the resilient member 3, as depicted in FIG. 4C. The surfaces of bore hole 13 of the resilient member are biased outwardly as the needle 16 is passed therethrough. Liquid drugs are injected from a syringe (not shown) through the needle 16 and into the reservoir 8 during filling. Once the reservoir 8 has been filled, the Teflon cannula 15 and needle 16 are removed, and the hole 13 is compressed closed to reseal the reservoir 8.

With the septum and method of the invention, the blunt needle 16 will enter the drug reservoir 8 through the same opening 13 each time, and that opening is formed in the manufacturing process, so that no destruction of the silicone rubber or polyurethane will occur due to punctures. Also, the cooperation of the protective shroud 5 of the casing 2 with the resilient member 3 permits the septum casing to be easily located under the skin and facilitates the placement of the needle into the septum using the two step procedure with the Teflon cannula 15, as referred to above. Therefore, the problems of material destruction leading to possible failure to contain liquid in the reservoir and difficulty in locating the septum have been obviated by the present invention.

While I have shown and described only one embodiment in accordance with the present invention, it is understood that the same is not limited thereto, but is susceptible of numerous changes and modifications as shown to those skilled in the art. Therefore, I do not wish to be limited to the details shown and described herein, but intend to cover all such changes and modifications as are encompassed by the scope of the appended claims.

I claim:

1. A method of making multiple re-entries in a septum implanted under the skin, the septum having a resilient member, support means for supporting the resilient member, the resilient member having a perforation therein which is compressed closed, and a protective shroud over a side of the resilient member, the protective shroud having a relatively large surface configured to channel the end of a slender, elongate component such as a needle to a predetermined location at a relatively small bore in the protective shroud which is located adjacent the perforation in the resilient member, comprising the steps of providing an assembly of a first needle and a cannula positioned over the first needle, penetrating the skin with said first needle and cannula thereon and contacting the the protective shroud with the end of said needle so as to channel the same to the small bore in the protective shroud, the small bore being dimensioned to prevent passage of the first needle through said shroud, withdrawing said first needle from the protective shroud and skin while leaving said cannula in place adjacent the small bore in said protective shroud, and inserting a second, relatively smaller needle into said cannula and through said small bore and the perforation in said resilient member.

2. A method according to claim 1, wherein said first needle is a 24 gauge needle and said second needle is a 27 gauge blunt cannula attached to a syringe.

3. A method according to claim , wherein said support means is connected to an implanted drug reservoir, and wherein said reservoir is filled with the drug from a syringe via said second needle.

4. A method according to claim 1, wherein said cannula is formed of Teflon.

* * * * *